United States Patent [19]
Marble

[11] Patent Number: 5,606,091
[45] Date of Patent: Feb. 25, 1997

[54] PREPARATION OF SYMMETRICAL OR UNSYMMETRICAL DISUBSTITUTED N-CYANODITHIOIMINOCARBONATES

[75] Inventor: Lyndon K. Marble, Germantown, Tenn.

[73] Assignee: Buckman Laboratories International, Inc., Memphis, Tenn.

[21] Appl. No.: 62,551

[22] Filed: May 18, 1993

[51] Int. Cl.$^6$ .................................................. C07C 329/16
[52] U.S. Cl. ........................................................... 558/2
[58] Field of Search ..................................... 558/2

[56] References Cited

U.S. PATENT DOCUMENTS

| | | | |
|---|---|---|---|
| 2,816,136 | 12/1957 | Pera | 558/2 |
| 2,881,070 | 4/1959 | Pera | 558/2 |
| 2,881,071 | 4/1959 | Buckman et al. | 558/2 |
| 3,299,129 | 1/1967 | D'Amico | 558/2 |
| 3,658,901 | 4/1972 | Timmons et al. | 558/2 |
| 4,543,309 | 9/1985 | Hirabayashi et al. | 430/31 |
| 5,068,347 | 11/1991 | Puckett et al. | 548/213 |

FOREIGN PATENT DOCUMENTS

| | | |
|---|---|---|
| 221221 | 1/1986 | Czechoslovakia . |
| 0142152 | 5/1985 | European Pat. Off. . |
| 181743 | 4/1985 | Hungary . |
| 1232838 | 5/1971 | United Kingdom . |

OTHER PUBLICATIONS

Hantzsch and Wolvekamp, Liebigs Ann. Chem. 331:265–97 (1904).
Wittenbrook, "The Chemistry of N–Cyanodithioimidocarbonic Acid. III. An Intermediate in Heterocyclic Synthesis," J. Heterocyclic Chem. 12:37–42 (1975).
Timmons and Wittenbrook, "The Chemistry of Cyanodithioimidocarbonic Acid," J. Org. Chem. 32:1566–72 (1967).
Suyama and Odo, "Synthetic Study of Cyanamidedithiocarbonic Acid Ester and Related Compounds (Part 1), " J. Syn. Org. Chem. (Japan) 29:65–73 (1971).
Trompen, Geevers and Hackmann, "Addition of Chlorine to the Cyanogen Bond IV," Rec. Trav. Chim. 90:463–68 (1971).
Wieland, Ph.D. dissertation, "A Nuclear Magnetic Resonance Study Part I. Conformational Inversion in 9,10-Dihydro-9,10-o-Xylyeneanthracene; Part II. Chemical Rate Processes of N–Cyanoimines," West Virginia University (1971).

D'Amico and Campbell, "Derivatives of Potassium Cyanodithioimidocarbonate. I. Synthesis of 1,4,6,9–Tetrathiaspiro[4.4]nonane and Related Compounds," J. Org. Chem. 32:2567–70 (1967).
Godfrey and Kurzer, "Heterocyclic Compounds from Urea Derivatives. Part I. A New Synthesis of 3–Amino–5–mercapto(and –hydroxy)–1,2,4–triazoles," J. Chem. Soc. (1960) pp. 3437–3444.
Thaler and McDivitt, "The Synthesis and Some Reactions of 1,2,4–Thiadiazolylsulfenyl Chlorides," J. Org. Chem. 36(1):14–18 (1971).
Wittenbrook, Smith and Timmons,"The Chemistry of N–Cyanodithioimido–carbonic Acid. II. Synthesis of 3–Halo–1,2,4–thiadiazoles," J. Org. Chem. 38(3):465–71 (1973).
Wobig, "Reaktioen von Cyanimidodithiocarbonaten und Cyanthioharnstoffsalzen mit γ–Bromocrotonsaure–derivaten," Liebigs Ann. Chem. (1978) pp. 1118–1122.
Leysen, Haemers and Bollaert, "Thiazolopyridine Analogs of Nalidixic Acid. 2. Thiazolo[4,5–b]pyridines," J. Heterocyclic Chem. 21:1361–66 (1984).
Krapivin, Jurasek, Kovac and Kul'nevich, "Synthesis and Properties of 4–Amino–5–(5–X–2–Furyl)Thiazole Derivatives," Collection Czechoslovak Chem. Commun. 49:2285–94 (1984).
Gattow and Klaeser, Z. Anorg. Allg. Chem. 433:211–16 (1977).

*Primary Examiner*—Paul J. Killos
*Assistant Examiner*—Dwayne C. Jones
*Attorney, Agent, or Firm*—Finnegan, Henderson, Farabow, Garrett & Dunner, L.L.P.

[57] ABSTRACT

A process which involves the step of contacting, in a methanolic solvent system, a metal salt, preferably a Group 1 or 2 metal salt, of the anion of formula II

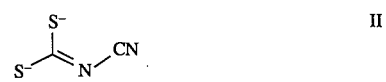

with at least one compound containing an R-group under conditions sufficient to form a symmetrical or unsymmetrical compound of formula I

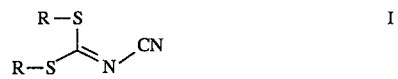

where the R-group is any suitable substituent group.

32 Claims, No Drawings

PREPARATION OF SYMMETRICAL OR UNSYMMETRICAL DISUBSTITUTED N-CYANODITHIOIMINOCARBONATES

FIELD OF THE INVENTION

The invention relates to processes for the preparation of symmetrical or unsymmetrical disubstituted N-cyanodithioiminocarbonates.

Broadly, the process of the invention involves the step of contacting, in a methanolic solvent system a metal salt of the anion of formula II

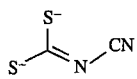

II with at least one compound containing an R-group under conditions sufficient to form a symmetrical or unsymmetrical compound of formula I

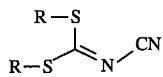

I where the R-group is any suitable substituent group.

BACKGROUND OF THE INVENTION

Disubstituted N-cyanodithioiminocarbonates have utility as intermediates in organic synthesis. For example, dimethyl N-cyanodithioiminocarbonate is an intermediate in the preparation of H2-antihistamines, such as cimetidine. Dimethyl N-cyanodithioiminocarbonate is also used in the manufacture of antiulcer and antisecretory compounds and is an intermediate in the preparation of many heterocycles.

Hantzsch and Wolvekamp, *Liebigs Ann. Chem.* 331:265 (1904) and Timmons and Wittenbrook, *J. Org. Chem.* 32:1566 (1967) describe the preparation of dimethyl N-cyanodithioiminocarbonate by the methylation of dipotassium N-cyanodithioiminocarbonate. The process of Timmons and Wittenbrook involves the methylation of the dipotassium N-cyanodithioiminocarbonate in aqueous acetone with one equivalent of methyl iodide. The potassium methyl N-cyanodithioiminocarbonate product is then isolated in about 95% yield. Then, the potassium methyl N-cyanodithioiminocarbonate is treated with another equivalent of methyl iodide in acetone which produces dimethyl N-cyanodithioiminocarbonate in about 58% yield.

Wittenbrook, *J. Heterocyclic Chem.* 12:37 (1975) describes the preparation of dimethyl N-cyanodithioiminocarbonate from the dipotassium salt of N-cyanodithioiminocarbonic acid by a simultaneous addition of two molar equivalents of methyl iodide to an acetone suspension of the dipotassium salt of N-cyanodithioiminocarbonic acid. Hungarian Patent No. 181,743 (Reiter) describes a reaction with an aqueous ethanol solution of the dipotassium salt of N-cyanodithioiminocarbonic acid. Wieland, Ph.D. dissertation, West Virginia University (1971) describes a reaction with an ethanol suspension of the dipotassium salt of N-cyanodithioiminocarbonic acid. Suyama and Odo, *J. Syn. Org. Chem.*, Japan, 29:65 (1971) describe the addition of two molar equivalents of base to a suspension of carbon disulfide ($CS_2$), cyanamide ($H_2NCN$) and methyl iodide ($CH_3I$).

Walek, Preiss, and Dietzel, *Z. Chem.* 18(4):144 (1978) describe the preparation of dimethyl N-cyanodithioiminocarbonate by adding one equivalent of dimethyl sulfate to a mono-methyl N-cyanodithioiminocarbonate dissolved in acetone. Trompen, Geevers, and Hackmann, *Rec. Trav. Chim.* 90:463 (1971) describe a methylation of the dipotassium salt of N-cyanodithioiminocarbonic acid in water. Hungarian Patent No. 181743 (Reiter) describes a reaction with the addition of two molar equivalents of dimethyl sulfate or a methyl halide in a solvent of aqueous ethanol, aqueous 1-propanol or aqueous 2-propanol. Czechoslovakian Patent No. 221221 (Vejdelek et al.) describes the addition of two molar equivalents of a methyl halide or dimethyl sulfate in a solvent of aqueous ethanol, aqueous 1-propanol or aqueous 2-propanol.

For the purposes of the invention the term "symmetrical" characterizes a disubstituted N-cyanodithioiminocarbonate as having two identical substituent groups R. For the purposes of the invention the term "unsymmetrical" characterizes a disubstituted N-cyanodithioiminocarbonate as having two different substituent groups R. For example, a compound of the general formula I

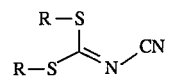

I may be a symmetrical or unsymmetrical compound because each R may be independently defined, for example, as any suitable substituent group. A compound of the following formula I-A

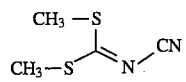

I-A is a symmetrical disubstituted N-cyanodithioiminocarbonate because both of the substituent groups are methyl. A compound of the following formula I-B

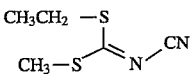

I-B is an unsymmetrical disubstituted N-cyanodithioiminocarbonate because one substituent group is methyl and the other substituent group is ethyl.

For the purposes of the invention, the term "metal salts" includes metal salts having monovalent, bivalent and fractions of polyvalent metals sufficient to balance the anionic charge in the salt. Mixed metal salts are also contemplated. Also, the term "metal hydroxide" includes hydroxides of monovalent, bivalent and fractions of polyvalent metals.

For the purposes of the invention, the term "Group 1 or Group 2 metals" includes all metals from Groups 1 and 2 of the Periodic Table.

Also, for the purposes of the invention, the term "methanolic solvent system" includes methanol, aqueous methanol, or any mixture of solvents including methanol. For example, a methanolic solvent system may include methanol and one or more other solvents, such as water, ethanol or acetone.

SUMMARY OF THE INVENTION

The invention provides a novel process for preparing symmetrical and unsymmetrical disubstituted N-cyanodithioiminocarbonates.

The invention can also provide a novel process for preparing a symmetrical or unsymmtetrical disubstituted N-cyanodithioiminocarbonate which can be rapid and efficient and which can provide good product yield and purity.

The invention further provides a method for preparing a symmetrical or unsymmetrical disubstituted N-cyanodithioiminocarbonate which can be efficiently performed on a large scale, including an industrial scale.

One aspect of the invention is a process involving the step of contacting, in a methanolic solvent system, a Group 1 or 2 metal salt of the anion of formula II

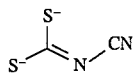
II with at least one compound containing an R-group under conditions sufficient to form a symmetrical or unsymmetrical compound of formula I

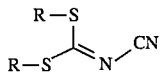
I where R is any suitable substituent group.

Another aspect of the invention is to provide a process which involves the steps of:

(a) contacting, in a methanolic solvent system, cyanamide, carbon disulfide, and a Group 1 or 2 metal hydroxide under conditions sufficient to produce a Group 1 or 2 metal salt of the anion of formula II

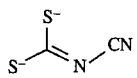
II and (b) contacting said Group 1 or 2 metal salt of the anion of formula II of (a) with at least one compound containing an R-group under conditions sufficient to form a symmetrical or unsymmetrical compound of formula I

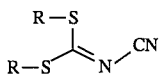
I where the R-group is any suitable substituent group.

A further aspect of the invention is a process which involves contacting, in a methanolic solvent system, a Group 1 or 2 metal salt of the anion of formula III

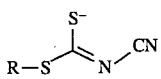
III with at least one compound containing an R-group under sufficient conditions to produce a symmetrical or unsymmetrical compound of formula I

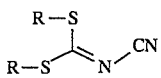
I where the R-group is any suitable substituent group.

The invention further provides a process which involves contacting, in a methanolic solvent system, a mono-alkaline metal salt of methyl N-cyanodithioiminocarbonate and a methylating agent under conditions sufficient to produce dimethyl N-cyanodithioiminocarbonate, where said alkaline metal is sodium or potassium.

The invention also provides a process which involves contacting, in a methanolic solvent system, a bis-alkaline metal salt of N-cyanodithioiminocarbonate and a methylating agent under conditions sufficient to produce dimethyl N-cyanodithioiminocarbonate, where said alkaline metal is sodium or potassium.

The invention also provides a large scale process which involves the step of contacting, preferably in a methanolic solvent system, a Group 1 or 2 metal salt of the anion of formula II

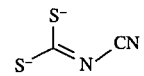
II with methyl chloride under conditions sufficient to form a compound of formula I-A

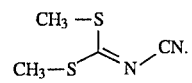
I-A

Other features and advantages of the invention will be set-forth in the description which follows, and in part will be apparent from the description, or may be learned by practice of the invention. The features and advantages of the invention may be realized and obtained by means of the processes set out in the appended claims.

DESCRIPTION OF PREFERRED EMBODIMENTS

The invention is directed to a process for the preparation of symmetrical or unsymmetrical disubstituted N-cyanodithioiminocarbonate. Symmetrical or unsymmetrical disubstituted N-cyanodithioiminocarbonates have utility as intermediates in organic synthesis.

A process according to the invention for the preparation of a symmetrical or unsymmetrical disubstituted N-cyanodithioiminocarbonate may involve the step of contacting, in a methanolic solvent system, a Group 1 or 2 metal salt of the anion of formula II

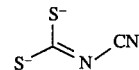
II with at least one compound containing an R-group under conditions sufficient to form a symmetrical or unsymmetrical compound of formula I

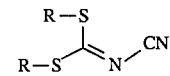
I where the R-group is any suitable substituent group. Preferably, the compound or compounds containing an R-group contacted with the Group 1 or 2 metal salt of the anion of formula II provide at least two molar equivalents of the group R. The total amount of the compound or compounds containing an R-group may be contacted with the Group 1 or 2 metal salt of the anion of formula II at about the same time. Alternatively, the compound or compounds containing an R-group may be added in multiple addition steps, preferably two addition steps.

In a preferred embodiment, R—X is a compound containing an R-group and M is a cation or cations from the GroUp I or Group II metals which balance the anionic charge. This process may be depicted as follows:

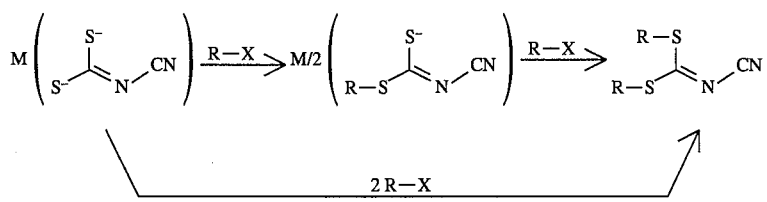

As shown in the above diagram, and according to the invention, the preparation of a symmetrical or unsymmetrical disubstituted N-cyanodithioiminocarbonate may be accomplished by either of the alternative reaction schemes.

A preferred embodiment of the invention is a process involving the steps of:

(a) contacting, in a methanolic solvent system, cyanamide, carbon disulfide, and a Group 1 or 2 metal hydroxide under conditions sufficient to produce a Group 1 or 2 metal salt of the anion of formula II

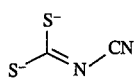   II (b) contacting said Group 1 or 2 metal salt of the anion of formula II of (a) with at least one compound containing an R-group under conditions sufficient to form a symmetrical or unsymmetrical compound of formula I

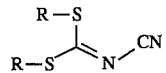   I where the R-group is any suitable substituent group.

In a preferred embodiment, R—X is a compound containing an R-group, M is a cation or cations from the Group I or Group II metals which balances the anionic charge, and $(3-n)M^{n+}(OH^-)_n$ is a Group I or II metal hydroxide where n is 1 or 2. This process may be depicted as follows:

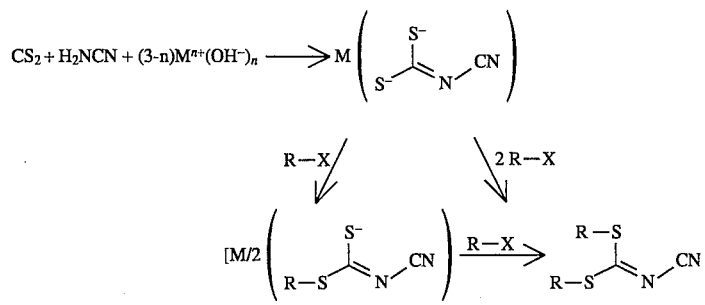

The invention also relates to a process which involves contacting, in a methanolic solvent system, a Group 1 or 2 metal salt of the anion of formula III

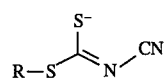   III with at least one compound containing an R-group under conditions sufficient to produce a symmetrical or unsymmetrical compound of formula I

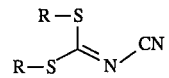   I where the R-group is any suitable substituent group. Preferably, the compound or compounds containing an R-group provide at least one molar equivalent of the group R and less than two molar equivalents of the group R.

In a preferred embodiment, R—X is a compound containing an R-group and M is a cation or cations from the Group I or Group II metals which balance the anionic charge. This process may be depicted as follows:

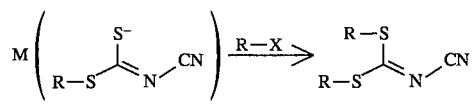

Another preferred embodiment of the invention is a process which involves contacting, in a methanolic solvent system, a bisalkaline metal salt of the anion of formula II

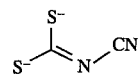   II with at least one compound containing an R-group under conditions sufficient to produce a compound of formula I

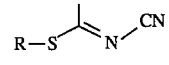   I where the R-group is any suitable substituent group. Preferably the compound or compounds containing an R-group provide at least two molar equivalents of the group R.

In a preferred embodiment, R—X is a compound containing an R-group and M is a cation or cations from the Group I or Group II metals which balances the anionic charge. This process may be depicted as follows:

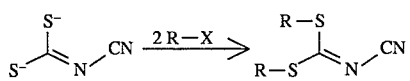

The above reactions of the invention and their preferred reactants and conditions are detailed below.

Preparation of Metal Salts of N-cyanodithioiminocarbonates

Metal salts of N-cyanodithioiminocarbonates have been prepared by various methods, such as contacting cyanamide and carbon disulfide, in a solvent of aqueous ethanol, water or absolute ethanol, with a solution of a metal hydroxide. For example, Timmons and Wittenbrook, *J. Org. Chem.*, 32, 1566 (1967) refer to a preparation of a metal salt of N-cyanodithioiminocarbonate in which solid cyanamide and solid potassium hydroxide react in ethanol followed by isolation of the precipitated solid product. Wieland, Ph.D. dissertation, West Virginia University (1971), and D'Amico and Campbell, *J. Org. Chem.*, 32, 2567 (1967) describe a process involving the reaction of aqueous cyanamide and aqueous KOH in 85–90% ethanol followed by isolation of the precipitated solid. Hungarian Patent No. 181,743 (Reiter) describes the reaction of aqueous cyanamide and aqueous KOH in 60% ethanol followed by isolation of the dipotassium salt product. U.S. Pat. No. 2,816,136 (Pera) refers to the reaction of alkali or alkaline earth metal hydroxides and alkali or alkaline earth metal cyanamides in an all-aqueous system.

According to the invention, the preparation of a Group 1 or 2 metal salt of N-cyanodithioiminocarbonate may involve contacting cyanamide, carbon disulfide, and a Group 1 or 2 metal hydroxide, in a methanolic solvent system, under conditions sufficient to produce a Group 1 or 2 metal salt of the anion of formula II

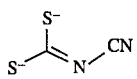
II

In a preferred method according to the invention, a solution of aqueous cyanamide and carbon disulfide is contacted with a Group 1 (alkaline) metal hydroxide, in a methanolic solvent system, to produce a bis-alkaline metal salt of N-cyanodithioiminocarbonate.

The preferred methanolic solvent system may be methanol, aqueous methanol, or any mixture of solvents including methanol. For example, a methanolic solvent system may include methanol and one or more other solvents, such as water, ethanol or acetone. Preferably, the amount of methanol in the reaction mixture is at least 25% of the total volume, excluding the carbon disulfide volume. More preferably, the amount of methanol in the reaction mixture is about 90% of the total volume, excluding the carbon disulfide volume. Most preferably, the amount of methanol, particularly on a large industrial scale, in the reaction mixture is about 50% of the total volume, excluding the carbon disulfide volume. Lower percentages of methanol may also be used. The reaction mixture containing a lower percentage of methanol may have some green or orange discoloration, which is not necessarily undesirable.

In a further preferred embodiment of the invention, a mixture of aqueous cyanamide, preferably in a 50% aqueous solution, and carbon disulfide ($CS_2$) in methanol, preferably 50% by volume of the total solution volume, excluding the $CS_2$ volume, is cooled preferably to 20° C. and a metal hydroxide, preferably a 50% aqueous solution, is added preferably over a 45 minute period. The reaction can be completed in about 2 hours. This reaction produces a yellow solution with a neutral to alkaline pH of generally 7–8.5.

The preferred use of a methanolic solvent system in the production of metal salts of N-cyanodithioiminocarbonate can be a significant improvement over other solvent systems. For example, the reaction for the production of a bis-alkaline metal salt of N-cyanodithioiminocarbonate may be performed in ethanol. However, a reaction in a methanolic solvent system possesses several advantages over a reaction in ethanol or other known solvents including, inter alia, a lower cost, a greater ease of separation from water for reuse, and a higher purity product.

These metal salts of N-cyanodithioiminocarbonates can be used in further reactions, for example, to produce a mono-alkaline metal salt of mono-substituted N-cyanodithioiminocarbonate or to produce a disubstituted N-cyanodithioiminocarbonate. The metal salts of N-cyanodithioiminocarbonates may be kept in the aqueous methanol reaction solution or they may be isolated prior to further reactions.

Preparation of Metal Salts of Mono-S-Substituted N-Cyanodithioiminocarbonates

A mono-S-substituted N-cyanodithioiminocarbonate has been prepared by a method reported by Timmons and Wittenbrook, *J. Org. Chem.*, 32:1566 (1967). In Timmons and Wittenbrook, potassium methyl N-cyanodithioiminocarbonate is prepared by adding a solution of methyl iodide in acetone at about 0° C. to an aqueous acetone solution of dipotassium N-cyanodithioiminocarbonate. The reaction mixture is concentrated, and the product is freed from the potassium iodide (KI) by-product-by dissolving the product in acetone and removing the KI by filtration. The acetone solution is concentrated and the solid product is washed with ether.

Using the processes according to the invention, the preparation of a metal salt of mono-S-substituted N-cyanodithioiminocarbonate can be more rapid and efficient than the prior art processes. The process of the invention may involve contacting, in a methanolic solvent system, a Group 1 or 2 metal salt of the anion of formula II

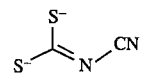
II with at least one compound containing an R-group under conditions sufficient to form a Group 1 or 2 metal salt of the anion of formula III

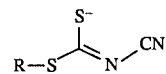
III where the R-group is ally suitable substituent group. Preferably, the compound or compounds containing an R-group provide at least one molar equivalent of the group R and less than two molar equivalents of the group R.

The methanolic solvent system may be methanol, aqueous methanol, or any mixture of solvents including methanol, as described above. Preferred methanolic solvent systems for the preparation of metal salts of mono-S-substituted N-cyanodithioiminocarbonates are the same as those described for the preparation of metal salts of N-cyanodithioiminocarbonates.

The group represented by R is preferably selected from substituted or unsubstituted, branched or unbranched $C_1$–$C_{20}$ alkyl, $C_2$–$C_{20}$ alkenyl or $C_2$–$C_{20}$ alkynyl groups; monocyclic or polycyclic, fused or nonfused, carbocyclic or heterocyclic, substituted or unsubstituted aryl groups; hydrogen; and non-aryl, monocyclic or polycyclic, fused or nonfused, substituted or unsubstituted heterocyclic groups; or R-S is preferably selected from thiosulfonates; sulfonates, thioesters and thiocarbamates. In a further preferred embodiment, R is selected from substituted or unsubstituted, branched or unbranched $C_1$–$C_6$ alkyl groups. More preferably, R is methyl, ethyl, propyl, or isopropyl, and most preferably, R is methyl.

In a preferred embodiment, the compound containing an R-group is a group R—X, where X is chloride, iodide, bromide or a group R—X—R, where X is a divalent group such as sulfate ($SO_4^{2-}$). For example, the compound containing an R-group may be selected from methylating agents $CH_3X$ and $(CH_3)_2X$, such as methyl chloride, methyl iodide, or dimethyl sulfate. In a preferred embodiment, the compound containing an R-group is methyl chloride.

In a preferred embodiment of the invention, an aqueous methanolic solution of a bis-alkaline metal salt of N-cyanodithioiminocarbonate, such as disodium N-cyanodithioiminocarbonate or dipotassium N-cyanodithioiminocarbonate, is treated with a compound containing an R-group, such as methyl chloride, dissolved in methanol or neat, preferably neat, until the reaction to prepare a mono-S-substituted N-cyanodithioiminocarbonate, such as sodium methyl N-cyanodithioiminocarbonate or potassium methyl N-cyanodithioiminocarbonate, is complete, generally about 2 hours. The reaction mixture can be concentrated to recover the methanol and isolate the reaction product.

Where the salt is a sodium salt, the sodium methyl N-cyanodithioiminocarbonate product can be obtained as a viscous yellow mixture which can contain NaCl. Where the salt is a potassium salt, the potassium methyl N-cyanodithioiminocarbonate product can be obtained as a yellow-white solid.

In a preferred embodiment, the mono-S-substituted N-cyanodithioiminocarbonate product can be purified with at least one solvent, such as acetone and/or dichloromethane, prior to any further reactions. A purification step may be performed to render the mono-S-substituted N-cyanodithioiminocarbonate product essentially, or totally, free of by-products.

The solid product may be freed from by-products, such as NaCl or KCl, by dissolving the product in a suitable solvent, such as acetone, and filtering. The solvent solution can then be concentrated to recover the solvent and, if concentrated, the resulting solid can be purified by suspending in a suitable solvent, such as dichloromethane, for a suitable time, such as 30 minutes, with agitation. The resultant slurry can then be filtered and the solid can be dried. Any disubstituted ester, such as the dimethyl ester, of N-cyanodithioiminocarbonate which may have formed during the reaction can be isolated from the filtrate.

The preferred use of dichloromethane for the purification is an improvement over the use of diethyl ether because, unlike diethyl ether, dichloromethane is not flammable and does not form peroxides. The product may then be dried either in air for about twelve hours or under vacuum at about 50° C. for about two hours.

These metal salts of mono-S-substituted N-cyanodithioiminocarbonate, which are preferably essentially free of contaminants, may be used in further reactions to produce, for example, symmetrical or unsymmetrical disubstituted N-cyanodithioiminocarbonates.

Preparation of Symmetrical or Unsymmetrical Disubstituted N-cyanodithioiminocarbonates Dimethyl N-cyanodithioiminocarbonate has been prepared, for example, by reacting dipotassium N-cyanodithioiminocarbonate with two molar equivalents of a methylating agent of methyl iodide or dimethyl sulfate, as noted above in the articles by Wittenbrook (1975), Suyama (1971), Trompen (1971), Reiter (1980) and Wieland (1971).

The process according to the invention involves the step of contacting, in a methanolic solvent system, a Group 1 or 2 metal salt of the anion of formula II

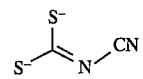     II with at least one compound containing an R-group under conditions sufficient to form a symmetrical or unsymmetrical compound of formula I

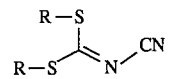     I where the R-group is any suitable substituent group.

The invention also relates to a process involving the steps of:

(a) contacting cyanamide, carbon disulfide, and at least one Group 1 or 2 metal hydroxide under conditions sufficient to produce a Group 1 or 2 metal salt of the anion of formula II

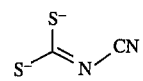     II (b) contacting said Group 1 or 2 metal salt of the anion of formula II of (a) with at least one compound containing an R-group under conditions sufficient to form a symmetrical or unsymmetrical compound of formula I

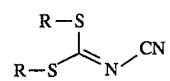     I where the R-group is any suitable substituent group. Either step (a) or (b), and preferably both steps (a) and (b), take place in a methanolic solvent system.

The invention also relates to the process which involves contacting, in a methanolic solvent system, a Group 1 or 2 metal salt of the anion of formula III

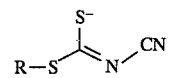     III with at least one compound containing an R-group under conditions sufficient to produce a symmetrical or unsymmetrical compound of formula I

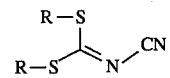     I where the R-group is any suitable substituent group. Preferably, the compound or compounds containing an R-group provide at least one molar equivalent of the group R and less than two molar equivalents of the group R.

The invention also involves the process which involves contacting, in a methanolic solvent system, a bis-alkaline metal salt of N-cyanodithioiminocarbonate and at least one compound containing an R-group under conditions sufficient to produce a symmetrical or unsymmetrical compound of formula I

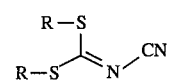     I where the R-group is any suitable substituent group. Preferably, the compound or compounds containing an R-group provide at least two molar equivalents of the group R.

The methanolic solvent system employed in the processes for the preparation of symmetrical or unsymmetrical disubstituted N-cyanodithioiminocarbonates may be methanol, aqueous methanol, or any mixture of solvents including methanol, as described above. Preferred methanolic solvent systems for the preparation of symmetrical or unsymmetrical disubstituted N-cyanodithioiminocarbonates are the same as those for the preparation of metal salts of N-cyanodithioiminocarbonates and metal salts of mono-S-substituted N-cyanodithioiminocarbonates, as described above.

In each of the processes for the preparation of symmetrical or unsymmetrical disubstituted N-cyanodithioiminocarbonates, the group R and the preferred embodiments of the group R, are the same as those described previously for the preparation of metal salts of mono-S-substituted N-cyanodithioiminocarbonates. As described above, in a particularly preferred embodiment, R is methyl, ethyl, propyl, or isopropyl, and most preferably, R is methyl.

In a preferred embodiment, the compound containing an R-group is a group R—X, where X is chloride, iodide, bromide or a group R—X—R, where X is a divalent group such as sulfate ($SO_4^{2-}$). For example, the compound containing an R-group may be selected from methylating agents $CH_3X$ and $(CH_3)_2X$, such as methyl chloride, methyl iodide, or dimethyl sulfate. In a further preferred embodiment, the compound containing an R-group is methyl chloride.

In a preferred embodiment of the invention, R is methyl and the disubstituted N-cyanodithioiminocarbonate is a dimethyl N-cyanodithioiminocarbonate. According to this embodiment of the invention, the novel preparation of dimethyl N-cyanodithioiominocarbonate can be more rapid and efficient than the prior art processes for its preparation. Dimethyl N-cyanodithioiminocarbonate can be produced in a high yield, preferably at least 70% yield and more preferably about 89% yield.

In another preferred embodiment of the invention, the preparation of dimethyl N-cyanodithioiminocarbonate involves contacting a mono-alkaline metal salt of methyl N-cyanodithioiminocarbonate with about one molar equivalent of methyl chloride in an aqueous methanolic solvent. Alternatively, a bis-alkaline metal salt of N-cyanodithioiminocarbonate is contacted with about two molar equivalents of methyl chloride in an aqueous methanolic solvent. The desired product can be isolated by concentrating the reaction mixture and extracting the product with a suitable organic solvent. The preferred inventive preparations involving methyl chloride can be efficient for large scale processes, including industrial scale processes.

In a further preferred embodiment, about 2.1 molar equivalents of methyl chloride gas are added to the solution of a bis-alkaline metal salt of N-cyanodithioiminocarbonate in an aqueous methanol solution while maintaining the temperature below 40° C. The reaction is then warmed to about 60° C., with an exotherm between about 55° and 60° C. as the temperature rises about 7° C. in 3 minutes. The temperature is held at about 60° C. for about 1.5 hours until the reaction is complete. The vessel is cooled to about 50° C. and the methanol is removed in vacuo. Dichloromethane is added to dissolve the product in an amount about equal to the amount of methanol used initially in the preparation of the dipotassium salt of N-cyanodithioiminocarbonate. The reactor is cooled to about 35° C. and the dichloromethane layer is removed.

The extraction process can be repeated until essentially all of the dimethyl N-cyanodithioiminocarbonate is removed from the reaction mixture. The organic layer may be dried, filtered and concentrated at 50° C. to give a yellow-orange oil. The oil may be dried under high vacuum at room temperature for 1 hour during which time it solidifies into a pale yellow solid.

The following examples are illustrative of the invention and are not intended to limit the scope of the invention.

Disodium N-Cyanodithioiminocarbonate

EXAMPLE 1

Cyanamide (40.5 g of 50% aqueous solution, 482 mmol, 1.0 equiv), 95% ethanol (96 mL), and carbon disulfide (36.6 g, 481 mmol, 1.0 equiv) were charged into a 1-L, three-necked, round-bottomed flask fitted with a thermometer, mechanical stirring paddle, addition funnel and nitrogen valve. The vessel was then purged with nitrogen for 10 minutes. The mixture was agitated and cooled to 5° C. A solution of base was prepared separately. Sodium hydroxide (38.6 g, 965 mmol, 2.0 equiv) was dissolved in 550 mL 95% ethanol over ½ h and the solution was cooled to room temperature. The addition funnel was charged with this solution. The solution of base was added to the cooled cyanamide mixture over 25 minutes while maintaining a temperature of 9° C. The yellow product mixture was stirred for 1 hour, and then the insoluble material was removed by filtration. This solution of disodium N-cyanodithioiminocarbonate was used directly in a further reaction to produce sodium methyl N-cyanodithioiminocarbonate. Alternatively, this solution of disodium N-cyanodithioiminocarbonate may be used in a further reaction to produce a symmetrical or unsymmetrical disubstituted N-cyanodithioiminocarbonate.

EXAMPLE 2

Cyanamide (10.2 g of a 50% aqueous solution; 120.5 mmol, 1.0 equiv), 95% ethanol (60 mL), and carbon disulfide (9.24 g, 121.4 mmol, 1.01 equiv) were charged into a 100-mL, three-necked, round-bottomed flask fitted with a thermometer, nitrogen valve, an addition funnel (non-equalizing) and a stirring bar. The addition funnel was charged with sodium hydroxide (9.64 g, 241 mmol, 2.0 equiv) dissolved in 17 mL water. The cyanamide mixture was cooled to 1° C. and the base solution was added dropwise over 34 minutes. The final temperature was 10° C. and the temperature was allowed to rise to 15° C. over 1 hour. The mixture was concentrated in vacuo, and the residual water was chased with 95% ethanol (2×50 mL). The yellow-white solid was suspended in ethanol, stirred for 10 minutes and filtered to yield 5.4 g (27%) of the disodium N-cyanodithioiminocarbonate as a white powder. The filtrate was concentrated to yield 16 g of slightly wet product.

EXAMPLE 3

In addition to the methods listed in Examples 1 and 2, disodium N-cyanodithioiminocarbonate can be prepared in other solvents such as aqueous ethanol (25 to 60% water, preferably 50% water) or aqueous methanol (5 to 75% water, preferably 50% water) and at temperatures between 0° and 30° C.

Dipotassium N-Cyanodithioiminocarbonate

EXAMPLE 4

Cyanamide (125.6 g of a 50% aqueous solution, 1.496 mol, 1.0 equiv), 95% ethanol (350 mL), and carbon disulfide (123.15 g, 1.617 mol, 1.08 equiv) were charged into a 1-L stainless steel autoclave. The system was sealed and potassium hydroxide (14.0M, 213.7 mL, 2.992 mol, 2.0 equiv) was pumped in over 20 minutes while the reaction temperature was maintained at under 30° C.

Water (30 mL) and 95% ethanol (30 mL) were used as rinses for the hydroxide. The mixture was stirred for 2 h, and the resulting yellow slurry was used directly in a further reaction to produce potassium methyl N-cyanodithioiminocarbonate. Alternatively, this slurry of dipotassium N-cyanodithioiminocarbonate may be used in a further reaction to produce a symmetrical or unsymmetrical disubstituted N-cyanodithioiminocarbonate.

EXAMPLE 5

Cyanamide (15.16 g of a 50% aqueous solution, 180 mmol, 1.0 equiv), methanol (40 mL), and carbon disulfide (13.7 g, 180 mmol, 1.0 equiv) were charged into a 100-mL, three-necked, round-bottomed flask equipped with a stirring bar, thermometer, and addition funnel. The system was sealed and potassium hydroxide (14.0M, 25.7 mL, 360 mmol, 2.0 equiv) was added over 18 minutes while the reaction temperature was maintained at under 20° C. The mixture was stirred for 2 h and the resulting yellow slurry was tested for residual cyanamide, and its pH was determined. Since cyanamide remained (TLC) and the pH was greater than 12, carbon disulfide (3 mL) was added to give the reaction mixture a pH of 9 after 15 minutes. This slurry was used directly in a further reaction to produce potassium methyl N-cyanodithioiminocarbonate. Alternatively, this slurry of dipotassium N-cyanodithioiminocarbonate may be used in a further reaction to produce a symmetrical or unsymmetrical disubstituted N-cyanodithioiminocarbonate.

EXAMPLE 6

A 10 gal, stainless steel autoclave was charged with cyanamide (4.8 kg of a 50% aqueous solution, 57.09 mol, 1.0 equiv), 95% ethanol (13 L), and carbon disulfide (4.35 kg, 57.13 mol, 1.0 equiv). A solution of potassium hydroxide (13.0M, 8.7 L, 113.5 mol, 1.99 equiv) was added at a rate of 100 mL/min while the reactor temperature was kept at or below 30° C. The reaction was continued for two hours after the KOH addition. The pH of the reaction was adjusted from 12 to 8.5 by the addition of concentrated HCl (2.3 L) and the solution was stirred for 0.5 h. This slurry was used directly in a further reaction to produce potassium methyl N-cyanodithioiminocarbonate.

EXAMPLE 7

A 10-gal, stainless-steel autoclave was charged with cyanamide (4.8 kg of a 50% aqueous solution, 57.09 mol, 1.0 equiv), methanol (13 L), and carbon disulfide (4.35 kg, 57.13 mol, 1.0 equiv). A solution of potassium hydroxide (14.2M, 8.0 L, 113.6 mol, 1.99 equiv) was added at a rate of 130 mL/min while the reactor temperature was kept at or below 30° C. The reaction was continued for 1.75 h after the KOH addition. The pH of the reaction was adjusted from 11 to 9 by the addition of carbon disulfide (200 mL) and the solution was stirred for 0.5 h. This slurry was used directly in a further reaction to produce potassium methyl N-cyanodithioiminocarbonate.

Sodium Methyl N-Cyanodithioiminocarbonate

EXAMPLE 8

An aqueous solution of disodium N-cyanodithioiminocarbonate (prepared according to U.S. Pat. No. 2,816,136, which is incorporated herein by reference), 32% by weight in water, 100 mL, 197 mmol) was diluted with acetone (160 mL) and water (79 mL). The solution was cooled to 5° C. and a solution of methyl iodide (28.0 g, 197.3 mmol, 1.00 equiv) in acetone (80 mL) was added dropwise over 45 minutes. The mixture was stirred for 30 minutes at 5° C. and was warmed to room temperature over 3.5 hours. The mixture was concentrated to a yellow slurry with a mass of 57 g (30 g theoretical yield). The slurry could be used as is in a further reaction to produce dimethyl N-cyanodithioiminocarbonate or 3-mercapto-5-amino-(1H)-1,2,4-triazole. This slurry could also be used as is in a further reaction to produce a symmetrical or unsymmetrical disubstituted N-cyanodithioiminocarbonate assuming a 95% conversion to the S-methyl adduct. Alternatively, the compound can be isolated and identified by methods known in the art.

EXAMPLE 9

Example 8 was repeated using a methylating agent of dimethyl sulfate in place of methyl iodide, with the exception that the product sodium methyl N-cyanodithioiminocarbonate (57 g, as a yellow slurry) was converted to dimethyl N-cyanodithioiminocarbonate in a further reaction with a second equivalent of methyl iodide.

EXAMPLE 10

An aqueous solution of disodium N-cyanodithioiminocarbonate (prepared according to U.S. Pat. No. 2,816,136, which is incorporated herein by reference) (32% by weight in water, 250 mL, 493 mmol) was diluted with acetone (250 mL). Dimethyl sulfate (62.2 g, 493 mmol, 1.0 equiv.) was added dropwise over 12 minutes, and the reaction temperature was allowed to rise to 50° C. The mixture was stirred for 1 hour while the temperature gradually decreased to 25° C. After 1 h, the mixture was concentrated to a yellow slurry with a volume of 250 mL. The slurry was diluted with acetone (1 L), filtered to remove sodium methyl sulfate, and concentrated to a volume of 150 mL. The slurry could be used as is in a further reaction to produce dimethyl N-cyanodithioiminocarbonate or 3-mercapto-5-amino-(1H)-1,2,4-triazole. This slurry could also be used as is in a further reaction to produce a symmetrical or unsymmetrical disubstituted N-cyanodithioiminocarbonate, assuming a 95% conversion to the S-methyl adduct. Alternatively, the compound can be isolated and identified by using methods known in the art.

EXAMPLE 11

Example 10 was repeated using a reaction temperature of 5° C., with the exception that the addition of dimethyl sulfate required 50 minutes. The slurry can be used as is in a further reaction to produce dimethyl N-cyanodithioiminocarbonate or 3-mercapto-5- amino-(1H)-1,2,4-triazole. The slurry could also be used to produce a symmetrical or unsymmetrical disubstituted N-cyanodithioiminocarbonate, assuming a 95% conversion to the S-methyl adduct. Alternatively, the compound can be isolated and identified by methods known in the art.

EXAMPLE 12

In addition to the methods listed in Examples 8–11, sodium methyl N-cyanodithioiminocarbonate can be prepared in solvents such as aqueous ethanol (5 to 75% water, preferably 50% water) and at temperatures between 0° and 50° C. Furthermore, other methylating agents, such as dimethyl sulfate or methyl chloride, could be used in place of methyl iodide.

Potassium Methyl N-Cyanodithioiminocarbonate

EXAMPLE 13

Dipotassium N-cyanodithioiminocarbonate (348.2 g, 1.794 mol, 1.0 equiv), water (1.575 L), and acetone (1.450 L) were charged into a 5-L, three-necked, round-bottomed flask equipped with a mechanical stirrer, thermometer, a fritted glass inlet tube and an exit tube. The solution was cooled to 3° C. and methyl chloride (102.8 g, 2.036 mol, 1.13 equiv) was added over 70 minutes while the temperature was maintained at less than 7° C. The reaction mixture was stirred overnight and then concentrated to give a wet yellow-white paste which was suspended in acetone (1.25 L, 4 mL/g of product) and stirred for 5 minutes. The mixture was filtered to yield 124 g (93%) of white potassium chloride. A sample of this solid was dissolved in water to give a clear colorless solution indicating that all the starting dipotassium salt had been consumed. The filtrate was concentrated in vacuo at 50° C. to a yellow-white solid, which was suspended in methylene chloride (900 mL, 3 mL/g of product) to remove dimethyl N-cyanodithioiminocarbonate side product and was stirred for about 30 minutes. The solid was collected by filtration, washed with methylene chloride (100 mL) and dried to yield 235 g (77%) of a white, crystalline solid (mp: 212°–217° C.). The $^1$H NMR was consistent with the structure. The methylene chloride filtrate was washed with water (100 mL), dried (MgSO$_4$), filtered and concentrated to yield 7.6 g (5.8%) of dimethyl N-cyanodithioiminocarbonate.

EXAMPLE 14

Cyanamide (15.1 g of a 50% aqueous solution, 180 mmol, 1.0 equiv), 95% ethanol (36 mL), and carbon disulfide (13.7 g, 180 mmol, 1.0 equiv) were charged into a 250-mL, three-necked round-bottomed flask equipped with a stirring bar, thermometer, and addition funnel. Potassium hydroxide (23.74 g, 360 mmol, 2.0 equiv, in 120 mL of 20% aqueous ethanol) was charged to the addition funnel and was added over 38 minutes while the reaction temperature was maintained at about 8° C. The mixture was stirred for 2.5 h and to the resulting slurry was added methyl chloride (12.6 g, 249 mmol, 1.38 equiv) over 1 h while the temperature rose to 45° C. The reaction mixture was stirred 1 h and was concentrated to a yellow-white paste. Acetone (125 mL; 4/g of product) was added to the paste and the mixture was stirred for 30 minutes. The mixture was filtered to yield 16.2 g of wet, white potassium chloride. A sample of this solid was dissolved in water to give a clear, colorless solution indicating that all the starting dipotassium salt had been consumed. The filtrate was concentrated at 50° C. to a yellow-white solid, which was suspended in methylene chloride (200 mL; 3 mL/g of product; to remove dimethyl N-cyanodithioiminocarbonate side product) and was stirred for about 30 minutes. The solid was collected by filtration, washed with methylene chloride (10 mL) and dried to yield 26.0 g (85%) of a faint pink crystalline solid which is potassium methyl N-cyanodithioiminocarbonate. The methylene chloride filtrate was concentrated to yield 1.7 g (9%) of dimethyl N-cyanodithioiminocarbonate.

EXAMPLE 15

Cyanamide (125.4 g of a 50% aqueous solution, 1.491 mol, 1.0 equiv), 95% ethanol (350 mL), and carbon disulfide (120 g, 1.576 mol, 1.05 equiv) were charged into a 1-L stainless steel autoclave. The system was sealed and potassium hydroxide (14.0M, 214.8 mL, 3.007 mol, 2.0 equiv) was pumped in over 20 minutes while the reaction temperature was maintained at under 30° C. Water (30 mL) was used as a rinse for the injection tube to insure that all the hydroxide had reached the reaction mixture. The mixture was stirred for 3 h and then methyl chloride (91.7 g, 1.82 mol, 1.21 equiv) was added over 1.75 h while a reaction temperature of 40° C. was maintained. After 45 minutes, the reaction mixture was concentrated to ⅔ volume and was divided into three 220 mL portions. Portion A was concentrated to a yellow-white paste which was suspended in acetone (340 mL; at 4 mL/g of product), stirred for 30 minutes and filtered. Wet potassium chloride was obtained (about 40 g) and the filtrate was concentrated to yield 75.3 g (88.6%) of potassium methyl N-cyanodithioiminocarbonate after drying for 2 h in a vacuum oven. Portion B was stored overnight and concentrated to a yellow-white paste. The water was chased with 95% ethanol (50 mL), and the paste was suspended in acetone (320 mL) and stirred for 0.5 h. The mixture was filtered to yield wet potassium chloride and the yellow filtrate was dried (Na$_2$SO$_4$), filtered and concentrated. The yield of dry product was 73.3 g (86%) as a granular yellow solid. This treatment of the product indicated that there was little decomposition of the potassium methyl adduct upon storage in the reaction mixture for about 12 hours.

EXAMPLE 16

Cyanamide (125.4 g of a 50% aqueous solution, 1.491 mol, 1.0 equiv), methanol (350 mL), and carbon disulfide (127.6 g, 1.676 mol, 1.12 equiv) were charged into a 1-L stainless steel autoclave. The system was sealed and potassium hydroxide (14.0M, 210 mL, 2.982 mol, 2.0 equiv) was pumped in over 20 minutes while the reaction temperature was maintained at under 25° C. Water (30 mL) was used as a rinse for the injection tube to insure that all the hydroxide had reached the reaction mixture. The mixture was stirred for 2 h and analysis of the reaction mixture indicated complete consumption of the cyanamide had occurred and that the pH was 7.5. Methyl chloride (75 g, 1.485 mol, 1.04 equiv) was added over 15 minutes while a reaction temperature of 35° C. was maintained. After 1.25 h, the reaction mixture was concentrated to a yellow-white paste. The water was chased with 95% ethanol (100 mL) and the paste was suspended in methanol (500 mL) and stirred for 0.5 h. The mixture was filtered to yield potassium chloride (dried by vacuum, 105 g, 95%), the filter case was washed with methanol (2×100 mL), and the yellow filtrate was concentrated. The resulting yellow paste was washed with methylene chloride (750 mL) and filtered. Analysis (TLC) of the potassium chloride solid and methylene chloride filtrate indicated that product was present in both.

The potassium chloride was washed with acetone (100 mL) and filtered. The methylene chloride filtrate was concentrated and the yellow-white paste was dissolved in acetone (375 mL) and filtered to remove a small amount of potassium chloride.

The acetone layers were combined and concentrated and the yellow-white paste was suspended in methylene chloride (300 mL) for 0.5 h. The mixture was filtered and the filter cake was washed with methylene chloride (100 mL) to yield 106 g KCl (95%) and 232 g (91%) of the desired potassium methyl product as a yellow-white powder (mp: 207° C.). The product was identified by $^1$H and $^{13}$C NMR spectra.

EXAMPLE 17

The aqueous ethanolic solution of dipotassium N-cyanodithioiminocarbonate as prepared in Example 6 was treated with methyl chloride (3.0 kg, 59.4 mol, 1.04 equiv) over 40 min at 40° C. and the mixture was stirred for 3 days. The reaction mixture was concentrated at 50° C. and 85 mm Hg and the residual water was chased with ethanol (4 L). The residue was washed with acetone (3×12 L) and the remaining solid KCl was suspended in acetone, filtered, and rinsed with acetone. The acetone was removed in vacuo to give a yellow solid which was stirred in dichloromethane (15 L) and filtered. The resulting solid was washed with dichloromethane again (12 L), filtered and dried to afford 5.45 kg (56%) of a golden yellow solid.

EXAMPLE 18

The aqueous methanolic solution of dipotassium N-cyanodithioiminocarbonate as prepared in Example 7 was treated with methyl chloride (2.9 kg, 57.4 mol, 1.006 equiv) over 30 min at 40° C. and the mixture was stirred for 3 days. The reaction mixture was concentrated at 50° C. and 85 mm Hg and the residual water slurry was concentrated in a tray dryer at 40° C. and 24 mm Hg for 44 h. The crude product was dissolved in acetone (39 L), filtered to remove the KCl, and concentrated at 32° C. and 75 mm Hg for 15 h in a tray dryer. The yellow solid was dispersed in dichloromethane (25 L), filtered, washed with more dichloromethane (5 L) and dried (18 h, 32° C., 50 mm Hg) to produce 7.73 kg (79%) of a yellow solid.

Dimethyl N-Cyanodithioiminocarbonate

EXAMPLE 19

To a solution of sodium methyl N-cyanodithioiminocarbonate (28.83 g, 187 mmol, prepared as in Example 8) diluted with acetone (180 mL) in a 500-mL, three-necked flask equipped with a mechanical stirring paddle, thermometer, nitrogen valve and an addition funnel was added dimethyl sulfate (23.6 g, 187.2 mmol, about 20 mL, 1.0 equiv) at 5° C. over 25 min. The cooling bath was removed and the resulting slurry was stirred at room temperature for 2.5 h. The slurry was concentrated to remove all the acetone and some of the residual water. The thick yellow oil was stirred rapidly in the residual water until it had cooled and solid had formed. The solid was isolated by filtration and air dried to yield 24.2 g (88%) of the dimethyl ester as a yellow-green solid. The melting point was 47°–52° C. and the product was further identified by $^1$H NMR.

EXAMPLE 20

To a suspension of dipotassium N-cyanodithioiminocarbonate prepared according to D'Amico (5.0 g, 25.72 mmol, 1.00 equiv) in acetone (21 mL) in a 50-mL, two-necked flask equipped with a magnetic stirring bar, thermometer, and Claisen adaptor fitted with a septum and nitrogen valve, was added dimethyl sulfate (6.48 g, 51.38 mmol, 2.00 equiv) via syringe at 4° C. over 5 min. The cooling bath was removed and the mixture was stirred for 1.5 h during which time the temperature reached a maximum of 33° C. The mixture was diluted with acetone (30 mL), filtered, concentrated and the residue dried to yield 3.25 g (87%) of a white solid having a melting point of 46°–47° C.

EXAMPLE 21

Potassium methyl N-cyanodithioiminocarbonate (523 g, 3.08 mol, 1.0 equiv), acetone (400 mL), and methyl chloride (195 g, 3.86 mol, 1.25 equiv) were charged to a 1-L stainless steel autoclave. The vessel was sealed and the mixture was warmed to 50° C. in about 0.5 h. The reaction began and an exotherm was observed as the temperature rose to 60° C. in 3 minutes. The mixture was held at 60° to 64° C. for 1 h and the vessel was cooled. The maximum pressure was 90 psi, when 60° C. was first attained, and the final pressure was 70 psi. The mixture was filtered, the vessel was rinsed with acetone (200 mL) and the isolated KCl was stirred with the wash acetone for 15 min and filtered. The recovery of KCl was 193 g (84%). The combined acetone layers were concentrated to a yellow slurry and dichloromethane (1100 mL; 3 mL/g) was added. The slurry was stirred for 30 min and filtered. The precipitated potassium methyl N-cyanodithioiminocarbonate (crude, 91 g, 17%) was removed by filtration and the filtrate was concentrated to yield the dimethyl ester as a yellow solid (277 g, 62%).

EXAMPLE 22

The temperature of a solution of dipotassium N-cyanodithioiminocarbonate prepared in aqueous methanol according to Example 16 was kept below 40° C. while methyl chloride (160 g, 3.17 mol, 2.58 equiv) was added as a gas over 10 minutes (final pressure= 100 psi). Once the methyl chloride was added, the reaction mixture was heated to 60° C. for 1.25 hours and then cooled. The reaction mixture was filtered to remove precipitated potassium chloride. The reaction vessel was rinsed with acetone (200 mL; methanol could also be used) and the isolated KCl was washed with acetone. The combined filtrates were concentrated in vacuo at 50° C. to remove the methanol and acetone. Dichloromethane (500 mL; 3 mL/g) was added and the mixture was stirred for 15 minutes while the temperature was decreased to 35° C. The organic layer was separated and the aqueous layer was extracted a second time in the same fashion. The organic layer was dried with sodium sulfate, filtered and concentrated in vacuo at 50° C. to give a viscous yellow-orange oil. The oil was dried and cooled under high vacuum (vacuum pump, 2.0 Torr) for 0.5 hour. The yield of the dimethyl ester as a yellow-white crystalline solid was 160 g (89%) with a melting point of 52°–53° C.

EXAMPLE 23

A solution of potassium methyl N-cyanodithioiminocarbonate (7.5 kg, 44.0 mol, 1.0 equiv; as prepared in Example 18) in methanol (6.1 L) was charged to a 10-gal, stainless-steel autoclave and treated with methyl chloride (2.93 kg, 58.0 mol, 1.32 equiv) over 58 min at 30° C. The temperature was raised to 50° C. and held at less than 64° C. for 1 h. The vessel was cooled and the reaction slurry was filtered to remove the KCl. The KCl was washed with methanol (6 L), filtered and rinsed with methanol (2 L). The recovery of KCl was 2.77 kg (85%). The filtrate was concentrated at about 60° C. and 150 mm Hg for 1 h. The residue was dissolved in dichloromethane (16.5 L), stirred and filtered to remove residual KCl. The filtrate was concentrated at 40° C. and 85 mm Hg for 23 h (heating for only 2 h) in a tray dryer to produce 5.73 kg (89%) of a yellow solid.

What is claimed is:

1. A process comprising the step of:

contacting, in a methanolic solvent system, a Group 1 or 2 metal salt of the anion of formula II

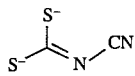

with at least one compound containing an R-group under conditions sufficient to form a symmetrical or unsymmetrical compound of formula I

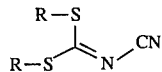

wherein the R-group is selected from substituted or unsubstituted, branched or unbranched up to $C_{20}$ alkyl, up to $C_{20}$ alkenyl or up to $C_{20}$ alkynyl groups;

monocyclic or polycyclic, fused or nonfused, carbocyclic substituted or unsubstituted aryl groups; or hydrogen;

or R—S is selected from thiosulfonates;

sulfonates;

thioesters; and thiocarbamates.

2. The process of claim 1, wherein said metal salt is a potassium or sodium salt.

3. The process of claim 1, wherein R is selected from substituted or unsubstituted, branched or unbranched $C_1$–$C_6$ alkyl groups.

4. The process of claim 1, wherein said methanolic solvent system is methanol or aqueous methanol.

5. The process of claim 4, wherein said methanolic solvent system further comprises ethanol or acetone.

6. The process of claim 1 wherein said compound containing an R-group is methyl chloride, dimethyl sulfate or methyl iodide.

7. The process of claim 1 wherein said compound of formula I is symmetrical and R is methyl.

8. A process comprising the steps of:

(a) contacting cyanamide, carbon disulfide, and a Group 1 or 2 metal hydroxide under conditions sufficient to produce a Group 1 or 2 metal salt of the anion of formula II

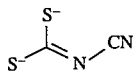

(b) contacting, in a methanolic solvent system, said Group 1 or 2 metal salt of the anion of formula II of (a) with at least one compound containing an R-group under conditions sufficient to form a symmetrical or unsymmetrical compound of formula I

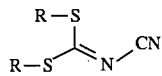

wherein the R-group is selected from substituted or unsubstituted, branched or unbranched up to $C_{20}$ alkyl, up to $C_{20}$ alkenyl or up to $C_{20}$ alkynyl groups;

monocyclic or polycyclic, fused or nonfused, carbocyclic substituted or unsubstituted aryl groups; or hydrogen;

or R—S is selected from thiosulfonates;

sulfonates;

thioesters; and thiocarbamates.

9. The process of claim 8, wherein said metal salt is a potassium or sodium salt.

10. The process of claim 9, wherein said salt of the anion of formula II produced in step (a) is not isolated prior to step (b).

11. The process of claim 9, wherein said salt of the anion of formula II produced in step (a) is isolated prior to step (b).

12. The process of claim 9, wherein R is selected from substituted or unsubstituted, branched or unbranched $C_1$–$C_6$ alkyl groups.

13. The process of claim 9, wherein said compound containing an R-group is methyl chloride, dimethyl sulfate or methyl iodide.

14. The process of claim 8, wherein said compound of formula I is symmetrical and R is methyl.

15. A process comprising the step of:

(c) contacting, in a methanolic solvent system, a Group 1 or 2 metal salt of the anion of formula III

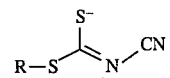

with at least one compound containing an R-group under conditions sufficient to produce a symmetrical or unsymmetrical compound of formula I

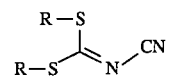

wherein the R-group is selected from substituted or unsubstituted, branched or unbranched up to $C_{20}$ alkyl, up to $C_{20}$ alkenyl or up to $C_{20}$ alkynyl groups;

monocyclic or polycyclic, fused or nonfused, carbocyclic substituted or unsubstituted aryl groups; or hydrogen;

or R—S is selected from thiosulfonates;

sulfonates;

thioesters; and thiocarbamates.

16. The process of claim 15, further comprising, prior to step (c), the steps of:

(a) contacting a solution of aqueous cyanamide and carbon disulfide and a Group 1 or 2 metal hydroxide under conditions sufficient to produce a Group 1 or 2 metal salt of the anion of formula II

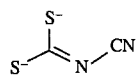

and (b) contacting the Group 1 or 2 metal salt of the anion of formula II of (a) with at least one compound containing an R group under conditions sufficient to produce a Group 1 or 2 metal salt of the anion of formula III

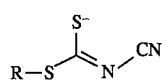

wherein the R-group is selected from
substituted or unsubstituted, branched or unbranched up to $C_{20}$ alkyl, up to $C_{20}$ alkenyl or up to $C_{20}$ alkynyl groups;

monocyclic or polycyclic, fused or nonfused, carbocyclic substituted or unsubstituted aryl groups; or hydrogen;

or R—S is selected from thiosulfonates;

sulfonates;

thioesters; and thiocarbamates.

17. The process of claim 17, wherein R is selected from substituted or unsubstituted, branched or unbranched $C_1$–$C_6$ alkyl groups.

18. The process of claim 15, wherein said compound containing an R-group is methyl chloride, dimethyl sulfate or methyl iodide.

19. The process of claim 18, wherein said compound containing an R-group is methyl chloride.

20. The process of claim 15, wherein said compound of formula I is symmetrical and R is methyl.

21. The process of claim 15, wherein in step (c), the compound or compounds containing the R-group provide at least one molar equivalent of the group R but less than two molar equivalents of the group R.

22. The process of claim 16, wherein said salt of the anion of formula II produced in step (a) is not isolated prior to step (b).

23. The process of claim 16, wherein said salt of the anion of formula II produced in step (a) is isolated prior to step (b).

24. The process of claim 16, further comprising the step of purifying said salt of the anion of formula III with at least one solvent prior to step (c).

25. The process of claim 24, wherein said purifying renders said salt of the anion of formula III essentially free of contaminants.

26. The process of claim 24, wherein said purification solvent is acetone or dichloromethane.

27. The process of claim 16, wherein said salt of the anion of formula III is sodium methyl N-cyanodithioiminocarbonate.

28. The process of claim 16, wherein said salt of the anion of formula III is potassium methyl N-cyanodithioiminocarbonate.

29. The process of claim 16, wherein in step (b) the compound or compounds containing the R-group provide at least one molar equivalent of the group R but less than two molar equivalents of the group R.

30. The process of claim 15, wherein contacting, in a methanolic solvent system, a sodium or a potassium salt of methyl N-cyanodithioiminocarbonate and a methylating agent to produce dimethyl N-cyanodithioiminocarbonate.

31. The process of claim 1, wherein contacting, in a methanolic solvent system, a sodium or potassium salt of N-cyanodithioiminocarbonate and a methylating agent to produce dimethyl N-cyanodithioiminocarbonate.

32. The process of claim 31, wherein said methylating agent is methyl chloride.

* * * * *

UNITED STATES PATENT AND TRADEMARK OFFICE
CERTIFICATE OF CORRECTION

PATENT NO. : 5,606,091
DATED : February 25, 1997
INVENTOR(S) : Lyndon K. Marble

It is certified that error appears in the above-indentified patent and that said Letters Patent is hereby corrected as shown below:

In claim 12, column 20, line 15, change "claim 9" to --claim 8--.

In claim 13, column 20, line 18, change "claim 9" to --claim 8--.

In claim 17, column 21, line 19, change "claim 17" to --claim 15--.

Signed and Sealed this

Twentieth Day of May, 1997

Attest:

BRUCE LEHMAN

Attesting Officer

Commissioner of Patents and Trademarks